(12) United States Patent
Fenko et al.

(10) Patent No.: US 9,702,617 B2
(45) Date of Patent: Jul. 11, 2017

(54) REFRIGERATOR APPLIANCE

(71) Applicant: General Electric Company, Schenectady, NY (US)

(72) Inventors: Anna Fenko, Louisville, KY (US); Brent Alden Junge, Evansville, IN (US)

(73) Assignee: Haier US Appliance Solutions, Inc., Wilmington, DE (US)

(*) Notice: Subject to any disclaimer, the term of this patent is extended or adjusted under 35 U.S.C. 154(b) by 40 days.

(21) Appl. No.: 14/933,150

(22) Filed: Nov. 5, 2015

(65) Prior Publication Data

US 2017/0131022 A1    May 11, 2017

(51) Int. Cl.
| | |
|---|---|
| *B01F 3/04* | (2006.01) |
| *F25D 23/12* | (2006.01) |
| *F25D 11/02* | (2006.01) |
| *B01F 3/22* | (2006.01) |
| *B01F 15/00* | (2006.01) |
| *C12M 1/107* | (2006.01) |

(52) U.S. Cl.
CPC ........ *F25D 23/126* (2013.01); *B01F 3/04106* (2013.01); *B01F 3/04787* (2013.01); *B01F 3/04808* (2013.01); *B01F 3/04815* (2013.01); *B01F 3/2223* (2013.01); *B01F 15/00162* (2013.01); *B01F 15/00344* (2013.01); *C12M 21/04* (2013.01); *F25D 11/02* (2013.01); *B01F 2003/049* (2013.01); *F25D 2323/122* (2013.01)

(58) Field of Classification Search
CPC .... B01F 3/04; B01F 3/04099; B01F 3/04106; B01F 3/04787; B01F 3/04808
USPC .............. 261/119.1, 121.1, DIG. 7; 99/323.1
See application file for complete search history.

(56) References Cited

U.S. PATENT DOCUMENTS

| | | | | |
|---|---|---|---|---|
| 3,552,726 | A | * | 1/1971 | Kraft ................... B01F 3/04808 222/129 |
| 4,850,269 | A | * | 7/1989 | Hancock ............. B01F 3/04241 261/140.1 |
| 5,848,736 | A | | 12/1998 | Boumann |
| 7,258,252 | B2 | | 8/2007 | Waters |
| 2012/0080445 | A1 | | 4/2012 | Moezidis et al. |

* cited by examiner

*Primary Examiner* — Robert A Hopkins
(74) *Attorney, Agent, or Firm* — Dority & Manning, P.A.

(57) ABSTRACT

A refrigerator appliance includes a beverage reservoir disposed within a chilled chamber of a cabinet. A conduit extends between a carbon dioxide source and the beverage reservoir. A controller is configured for activating the carbon dioxide source such that the carbon dioxide source directs carbon dioxide into the beverage reservoir via the conduit when liquid is dispensed from the beverage reservoir.

19 Claims, 3 Drawing Sheets

REFRIGERATOR APPLIANCE

FIELD OF THE INVENTION

The present subject matter relates generally to refrigerator appliances and beverage preservation within the same.

BACKGROUND OF THE INVENTION

Refrigerator appliances generally include a cabinet that defines a chilled chamber. Food items, including beverages and other liquids, may be stored within the chilled chamber. The low temperature of the chilled chamber relative to ambient atmosphere assists with increasing a shelf life of the food items stored within the chilled chamber.

Certain beverages, such as milk and juice, are frequently purchased in large volumes. Consuming the entire beverage prior to spoiling can be difficult. In addition, organic beverages can be difficult to store for long periods of time within refrigerator appliances. For example, raw milk and breast milk can be particularly difficult to store for long periods of time within refrigerator appliances.

Accordingly, a refrigerator appliance with features for increasing a shelf life of liquids within the refrigerator appliance would be useful. In particular, a refrigerator appliance with features for increasing a shelf life of large volume beverages within the refrigerator appliance would be useful.

BRIEF DESCRIPTION OF THE INVENTION

The present subject matter provides a refrigerator appliance. The refrigerator appliance includes a beverage reservoir disposed within a chilled chamber of a cabinet. A conduit extends between a carbon dioxide source and the beverage reservoir. A controller is configured for activating the carbon dioxide source such that the carbon dioxide source directs carbon dioxide into the beverage reservoir via the conduit when liquid is dispensed from the beverage reservoir. Additional aspects and advantages of the invention will be set forth in part in the following description, or may be apparent from the description, or may be learned through practice of the invention.

In a first exemplary embodiment, a refrigerator appliance is provided. The refrigerator appliance includes a casing that defines a chilled chamber. A beverage reservoir is disposed within the chilled chamber of the cabinet. A beverage preservation assembly includes a carbon dioxide source. A conduit extends between the carbon dioxide source and the beverage reservoir. An outlet of the conduit is positioned at a bottom portion of the beverage reservoir. A controller is operatively coupled to the carbon dioxide source. The controller is configured for activating the carbon dioxide source such that the carbon dioxide source directs carbon dioxide into the beverage reservoir via the conduit when liquid is dispensed from the beverage reservoir.

In a second exemplary embodiment, a refrigerator appliance is provided. The refrigerator appliance includes a casing that defines a freezer chamber and a fresh food chamber. A beverage reservoir is disposed within the fresh food chamber of the cabinet. A beverage preservation assembly includes a carbon dioxide source positioned within the cabinet. A conduit extends between the carbon dioxide source and the beverage reservoir. A valve is coupled to the conduit. A controller is operatively coupled to the valve. The controller is configured for opening the valve such that carbon dioxide from the carbon dioxide source flows into the beverage reservoir via the conduit when liquid is dispensed from the beverage reservoir.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

DETAILED DESCRIPTION

Figure 1:
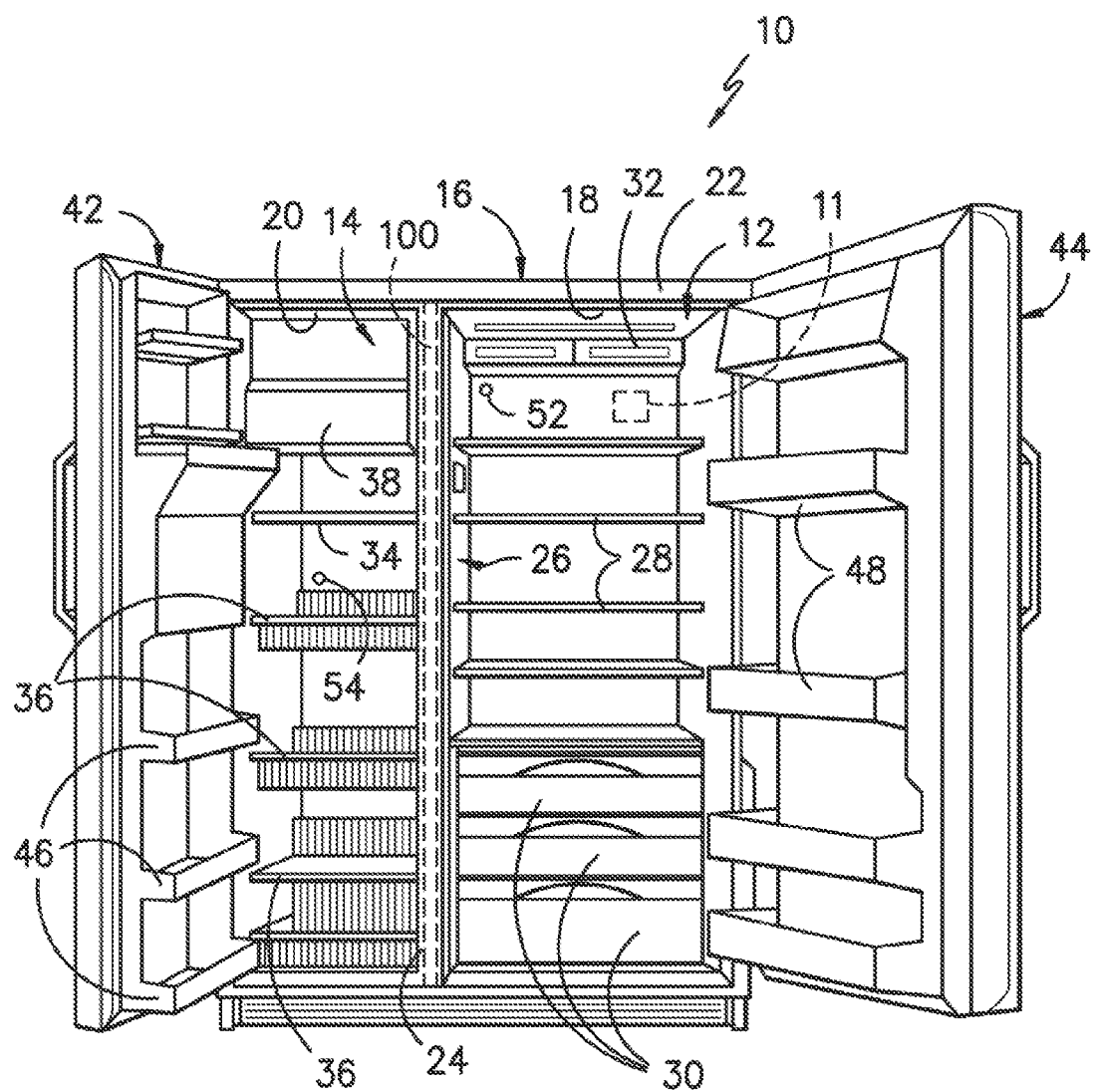
FIG. 1 provides a front view of a refrigerator appliance according to an exemplary embodiment of the present subject matter.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

FIG. 1 provides a front view of a representative refrigerator appliance 10 according to an exemplary embodiment of the present invention. More specifically, for illustrative purposes, the present invention is described with a refrigerator appliance 10 having a construction as shown and described further below. As used herein, a refrigerator appliance includes appliances such as a refrigerator/freezer combination, side-by-side, bottom mount, compact, and any other style or model of refrigerator appliance. Accordingly, other configurations including multiple and different styled compartments could be used with refrigerator appliance 10, it being understood that the configuration shown in FIG. 1 is by way of example only.

Refrigerator appliance 10 includes a fresh food storage compartment 12 and a freezer storage compartment 14. Freezer compartment 14 and fresh food compartment 12 are arranged side-by-side within an outer case 16 and defined by inner liners 18 and 20 therein. A space between case 16 and liners 18, 20 and between liners 18, 20 is filled with foamed-in-place insulation. Outer case 16 normally is formed by folding a sheet of a suitable material, such as pre-painted steel, into an inverted U-shape to form the top and side walls of case 16. A bottom wall of case 16 normally is formed separately and attached to the case side walls and to a bottom frame that provides support for refrigerator appliance 10. Inner liners 18 and 20 are molded from a suitable plastic material to form freezer compartment 14 and fresh food compartment 12, respectively. Alternatively, liners 18, 20 may be formed by bending and welding a sheet of a suitable metal, such as steel.

A breaker strip 22 extends between a case front flange and outer front edges of liners 18, 20. Breaker strip 22 is formed from a suitable resilient material, such as an extruded acrylo-butadiene-styrene based material (commonly referred to as ABS). The insulation in the space between liners 18, 20 is covered by another strip of suitable resilient material, which also commonly is referred to as a mullion 24. In one embodiment, mullion 24 is formed of an extruded ABS material. Breaker strip 22 and mullion 24 form a front face, and extend completely around inner peripheral edges of case 16 and vertically between liners 18, 20. Mullion 24, insulation between compartments, and a spaced wall of liners separating compartments, sometimes are collectively referred to herein as a center mullion wall 26. In addition, refrigerator appliance 10 includes shelves 28 and slide-out storage drawers 30, sometimes referred to as storage pans, which normally are provided in fresh food compartment 12 to support items being stored therein.

Refrigerator appliance 10 can be operated by one or more controllers 11 or other processing devices according to programming and/or user preference via manipulation of a control interface 32 mounted, e.g., in an upper region of fresh food storage compartment 12 and connected with controller 11. Controller 11 may include one or more memory devices and one or more microprocessors, such as a general or special purpose microprocessor operable to execute programming instructions or micro-control code associated with the operation of the refrigerator appliance. The memory may represent random access memory such as DRAM, or read only memory such as ROM or FLASH. In one embodiment, the processor executes programming instructions stored in memory. The memory may be a separate component from the processor or may be included onboard within the processor. Controller 11 may include one or more proportional-integral ("PI") controllers programmed, equipped, or configured to operate the refrigerator appliance according to exemplary aspects of the control methods set forth herein. Accordingly, as used herein, "controller" includes the singular and plural forms.

Controller 11 may be positioned in a variety of locations throughout refrigerator appliance 10. In the illustrated embodiment, controller 11 may be located e.g., behind an interface panel 32 or doors 42 or 44. Input/output ("I/O") signals may be routed between the control system and various operational components of refrigerator appliance 10 along wiring harnesses that may be routed through e.g., the back, sides, or mullion 26. Typically, through user interface panel 32, a user may select various operational features and modes and monitor the operation of refrigerator appliance 10. In one embodiment, the user interface panel may represent a general purpose I/O ("GPIO") device or functional block. In one embodiment, the user interface panel 32 may include input components, such as one or more of a variety of electrical, mechanical or electro-mechanical input devices including rotary dials, push buttons, and touch pads. The user interface panel 32 may include a display component, such as a digital or analog display device designed to provide operational feedback to a user. User interface panel 32 may be in communication with controller 11 via one or more signal lines or shared communication busses.

In one exemplary embodiment of the present invention, one or more temperature sensors are provided to measure the temperature in the fresh food compartment 12 and the temperature in the freezer compartment 14. For example, first temperature sensor 52 may be disposed in the fresh food compartment 12 and may measure the temperature in the fresh food compartment 12. Second temperature sensor 54 may be disposed in the freezer compartment 14 and may measure the temperature in the freezer compartment 14. This temperature information can be provided, e.g., to controller 11 for use in operating refrigerator 10 as will be more fully discussed below. These temperature measurements may be taken intermittently or continuously during operation of the appliance and/or execution of a control system as further described below.

A shelf 34 and wire baskets 36 are also provided in freezer compartment 14. In addition, an ice maker 38 may be provided in freezer compartment 14. A freezer door 42 and a fresh food door 44 close access openings to freezer and fresh food compartments 14, 12, respectively. Each door 42, 44 is mounted to rotate about its outer vertical edge between an open position, as shown in FIG. 1, and a closed position (not shown) closing the associated storage compartment. In alternative embodiments, one or both doors 42, 44 may be slidable or otherwise movable between open and closed positions. Freezer door 42 includes a plurality of storage shelves 46, and fresh food door 44 includes a plurality of storage shelves 48.

Figure 2:
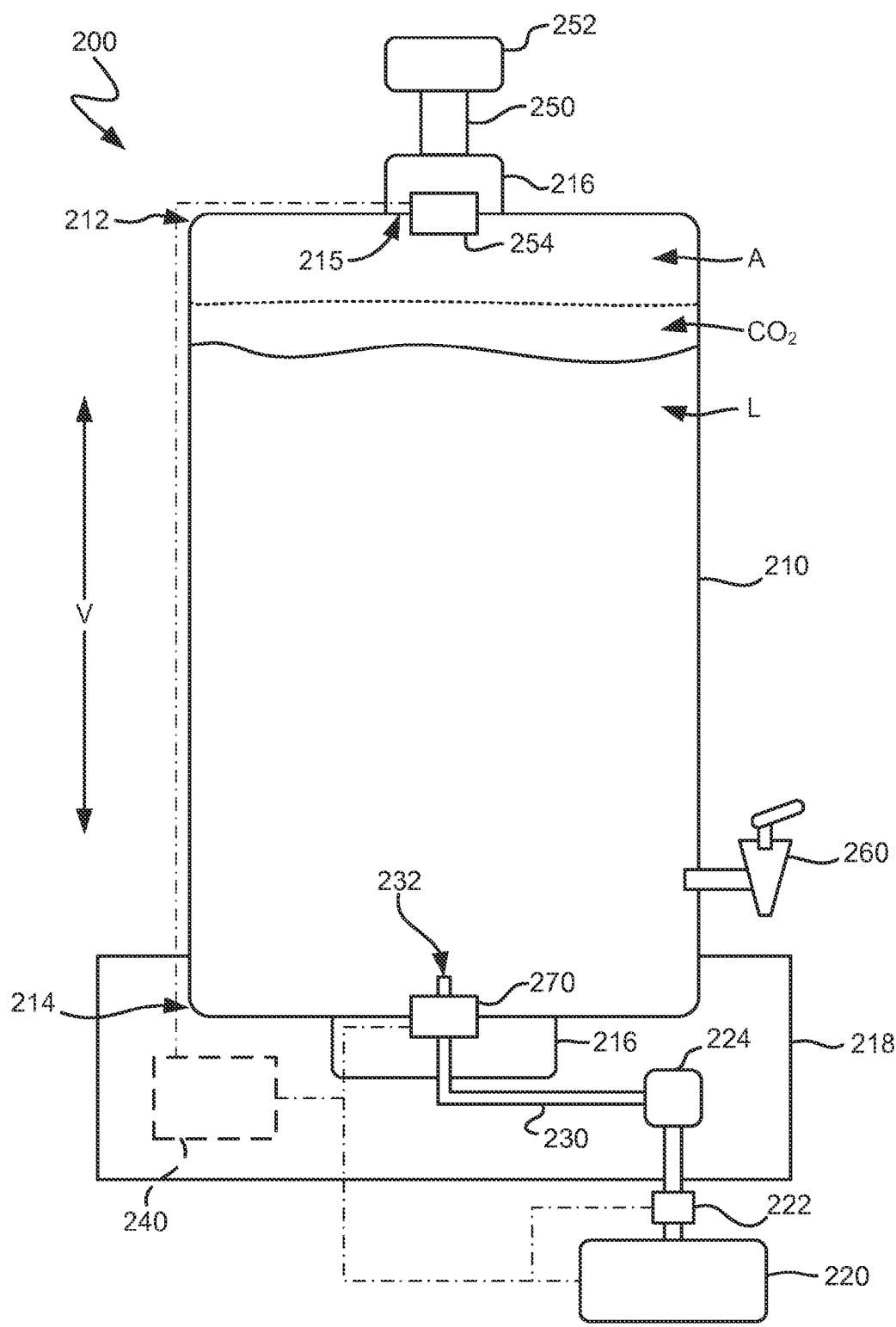
FIG. 2 provides a schematic view of a beverage preservation assembly according to an exemplary embodiment of the present subject matter.

FIG. 2 provides a schematic view of a beverage preservation assembly 200 according to an exemplary embodiment of the present subject matter. Beverage preservation assembly 200 may be used in or with any suitable refrigerator appliance. For example, beverage preservation assembly 200 may be used in refrigerator appliance 10. Thus, beverage preservation assembly 200 is discussed in greater detail below in the context of refrigerator appliance 10. As discussed in greater detail below, beverage preservation assembly 200 includes features for extending or increasing a shelf life of beverages within refrigerator appliance 10.

As shown in FIG. 2, beverage preservation assembly 200 includes a liquid or beverage reservoir 210. Beverage reservoir 210 may be positioned within a chilled chamber of refrigerator appliance 10, e.g., fresh food compartment 12. In particular, beverage reservoir 210 may be mounted to a base 218 that is positioned or mounted on fresh food door 44. Beverage reservoir 210 is configured for receiving and storing a liquid L therein. Any suitable liquid may be disposed or stored within beverage reservoir 210. For example, milk, juice, tea, soup, etc., may be stored within beverage reservoir 210. In certain exemplary embodiments, beverage reservoir 210 may be a container purchased pre-filled with a liquid therein, such as a milk jug, juice box, etc., at a store or other point of purchase. In other exemplary embodiments, beverage reservoir 210 may be a refillable container that a user of refrigerator appliance 10 may fill with a selected liquid for storage within beverage reservoir 210, e.g., home-made liquids, such as soup or juice, or breast milk. Beverage reservoir 210 may hold any suitable volume of liquid. For example, beverage reservoir 210 may hold at least one gallon of liquid therein.

A dispenser nozzle 260 may be mounted to beverage reservoir 210. Dispenser nozzle 260 is configured for selectively directing liquid out of beverage reservoir 210. As an example, dispenser nozzle 260 may be mounted to beverage reservoir 210 at bottom portion 214 of beverage reservoir 210 when beverage reservoir 210 is a refillable container. As another example, dispenser nozzle 260 may be mounted to cap 216 when beverage reservoir 210 is an original container.

Beverage reservoir 210 extends between a top portion 212 and a bottom portion 214, e.g., along a vertical direction V. Beverage reservoir 210 may define an opening 215 at or adjacent top portion 212 of beverage reservoir 210. A user may fill beverage reservoir 210 with liquid L via opening 215 at top portion 212 of beverage reservoir 210. It should be understood that opening 215 may be positioned at any other suitable location on beverage reservoir 210 in alternative exemplary embodiments. For example, opening 215 may be positioned at or adjacent bottom portion 214 of beverage reservoir 210. A cap 216 may be secured (e.g., threaded) to beverage reservoir 210 at opening 215 of beverage reservoir 210 in order to seal opening 215 of beverage reservoir 210 with cap 216.

If beverage reservoir 210 is an original container, such as a milk or juice plastic container, beverage reservoir 210 may be sealed or continuous at top portion 212 of beverage reservoir 210, e.g., because the original container may be inverted such that a bottom wall of the inverted original container is positioned at top portion 212 of beverage reservoir 210 shown in FIG. 2. If beverage reservoir 210 is a refillable container, the liquid L may be poured into beverage reservoir 210 via opening 215, e.g., without the need to flip beverage reservoir 210 as with original containers. After the liquid L is poured inside, cap 216 may be mounted to and seal beverage reservoir 210.

Beverage preservation assembly 200 also includes a carbon dioxide source 220. Carbon dioxide source 220 may be any suitable source or generator of carbon dioxide. For example, carbon dioxide source 220 may be a cartridge that is charged or filled with carbon dioxide gas or liquid. As another example, carbon dioxide source 220 may be a canister having a pallet of yeast and sugar therein. A chemical reaction between warm water and the pallet of yeast and sugar may generate carbon dioxide gas. The canister with the pallet of yeast and sugar may be a separate container that is attached to a one-way valve to control intake of carbon dioxide gas from carbon dioxide source 220 to beverage reservoir 210.

As discussed in greater detail below, carbon dioxide source 220 supplies carbon dioxide $CO_2$ to beverage reservoir 210 when liquid L is dispensed from beverage dispenser 210. Thus, carbon dioxide $CO_2$ from carbon dioxide source 220 may act as a rebalancing gas within beverage dispenser 210 to replace the volume of liquid dispensed from beverage reservoir 210. A conduit 230 extends between carbon dioxide source 220 and beverage reservoir 210. Carbon dioxide $CO_2$ may flow from carbon dioxide source 220 into beverage reservoir 210 via conduit 230. An outlet 232 of conduit 230 may be positioned at or adjacent bottom portion 214 of beverage reservoir 210. Thus, carbon dioxide exiting conduit 230 at outlet 232 of conduit 230 may pass or bubble through liquid L within beverage reservoir 210 such that at least a portion of the carbon dioxide $CO_2$ from outlet 232 of conduit 230 may dissolve within the liquid L.

Carbon dioxide $CO_2$ from carbon dioxide source 220, e.g., acting as a rebalancing gas, settles above the surface of the liquid L thereby displacing air A from the surface of the liquid L, as shown in FIG. 2, e.g., because the molecular weight of carbon dioxide is fifty-two percent (52%) higher than that of air. The separation or stratification between carbon dioxide $CO_2$ and air A within beverage reservoir 210 takes time, but eventually the air A is displaced to top portion 212 of beverage reservoir 210 (e.g., a bottom wall of an inverted original container). In certain exemplary embodiments, no air A is purposefully added to beverage reservoir 210 when liquid L is dispensed from beverage container 210. Rather, carbon dioxide $CO_2$ from carbon dioxide source 220 may flow into beverage dispenser 210 through liquid L to a head space above liquid L in order to equalize a pressure within the head space above liquid L with the carbon dioxide $CO_2$. In the head space above liquid L in beverage reservoir 210, the carbon dioxide $CO_2$ is positioned over the liquid L and hinders or limits oxidizing of the liquid L. Similarly, the dissolved carbon dioxide $CO_2$ within the liquid L in beverage reservoir 210 also hinders or limits oxidizing of the liquid L.

Beverage preservation assembly 200 also includes various sensors for monitoring operation of beverage preservation assembly 200. In particular, beverage preservation assembly 200 may include a first pressure (and/or carbon dioxide sensor) sensor 254, a second pressure sensor 222 and a pH sensor 270. First sensor 254, second pressure sensor 222 and pH sensor 270 are in operative communication with a controller 240 of beverage preservation assembly 200, such as controllers 11 of refrigerator appliance 10.

First pressure sensor 254 is configured for measuring a gas pressure within beverage reservoir 210. Thus, e.g., first pressure sensor 254 may output a signal to controller 240 corresponding to the pressure of gas within beverage reservoir 210. In addition, first sensor 254 may also be configured for measuring a carbon dioxide $CO_2$ concentration or amount within the head space of beverage reservoir 210. Thus, e.g., first sensor 254 may output a signal to controller 240 corresponding to the carbon dioxide $CO_2$ concentration or amount within the head space of beverage reservoir 210. First pressure sensor 254 may be positioned at or adjacent top portion 212 of beverage reservoir 210. In particular, first pressure sensor 254 may be extended from bottom portion 214 of beverage reservoir 210 through beverage reservoir 210 to top portion 212 of beverage reservoir 210 when beverage reservoir 210 is an original container. For example, first pressure sensor 254 may be mounted to cap 216 or to beverage reservoir 210 at top portion 212 of beverage reservoir 210. Second pressure sensor 222 is configured for measuring a gas pressure within or at carbon dioxide source 220. Thus, e.g., second pressure sensor 222 may output a signal to controller 240 corresponding to the pressure of gas within carbon dioxide source 220 and/or conduit 230. Second pressure sensor 222 may be coupled to carbon dioxide source 220 or conduit 230. pH sensor 270 is configured for measuring the pH of the liquid L within beverage reservoir 210. Thus, e.g., pH sensor 270 may output a signal to controller 240 corresponding to the pH of the liquid L within beverage reservoir 210. pH sensor 270 may be positioned at or adjacent bottom portion 214 of beverage reservoir 210.

Controller 240 may include a memory and one or more processing devices such as microprocessors, CPUs, or the like, such as general or special purpose microprocessors operable to execute programming instructions or microcontrol code associated with operation of beverage preservation assembly 200. The memory may represent random access memory such as DRAM or read only memory such as ROM or FLASH. In one embodiment, the processor executes programming instructions stored in memory. The memory may be a separate component from the processor or may be included onboard within the processor. Controller 240 may be in communication with various components of beverage preservation assembly 200 via one or more signal lines or shared communication busses.

Beverage preservation assembly 200 may also include various components for venting or removing the air A from beverage reservoir 210. In particular, as shown in FIG. 2, beverage preservation assembly 200 includes a check valve 250 and a gas separating membrane 252. Check valve 250 and gas separating membrane 252 are positioned at top portion 212 of beverage reservoir 210 and are in fluid communication with the head space of beverage reservoir 210. In particular, check valve 250 and gas separating membrane 252 may be mounted to cap 216 at opening 215 of beverage reservoir 210. Check valve 250 is configured for allowing or permitting the air A to exit beverage reservoir 210, e.g., when the pressure inside beverage reservoir 210 is greater than a pressure level. The pressure level may be selected as less than the pressure permissible to avoid liquid particle precipitation from the liquid L, such as proteins from milk. Thus, addition of carbon dioxide $CO_2$ from carbon dioxide source 220 may fill the additional head space above the liquid L during dispensing of the liquid L from beverage reservoir 210, and the carbon dioxide $CO_2$ may also slowly push the air A out of beverage reservoir 210 via check valve 250 and gas separating membrane 252 as the carbon dioxide $CO_2$ fills the head space of beverage reservoir 210 above the liquid L from beverage reservoir 210. In such a manner, the carbon dioxide $CO_2$ from carbon dioxide source 220 may further reduce oxygen concentration within beverage reservoir 210. Gas separating membrane 252 may insure that the air A is restricted or ejected slowly in order to avoid significant losses of carbon dioxide $CO_2$ from beverage reservoir 210.

Beverage preservation assembly 200 also includes a valve 224, such as a solenoid valve, coupled to conduit 230. Controller 240 is in operative communication with valve 224 and is configured for selectively opening and closing valve 224. When valve 224 is open, carbon dioxide $CO_2$ may flow from carbon dioxide source 220 into beverage reservoir 210 via conduit 230. Conversely, valve 224 may block or obstruct carbon dioxide $CO_2$ flow from carbon dioxide source 220 into beverage reservoir 210 via conduit 230 when valve 224 is closed. Controller 240 may be configured for opening valve 224 when a pressure measurement from first pressure sensor 254 is less than a threshold pressure (e.g., selected to correspond to liquid L dispensing from beverage reservoir 210). Thus, pressure decreases in the air A or carbon dioxide $CO_2$ in the head space over liquid L in beverage reservoir 210 may correspond to dispensing of liquid L from beverage reservoir 210, and controller 240 may open valve 224 in order to direct carbon dioxide $CO_2$ from carbon dioxide source 220 into beverage reservoir 210 via conduit 230 during dispensing of liquid L from beverage reservoir 210 in order to replace the dispensed liquid within beverage reservoir 210 with carbon dioxide $CO_2$ from carbon dioxide source 220. Controller 240 may also be configured for closing valve 224 when a pressure measurement from first pressure sensor 254 is greater than a pressure measurement from second pressure sensor 222, in order to avoid or prevent liquid flow from beverage reservoir 210 to carbon dioxide source 220 via conduit 230. Valve 224 may be a one-way valve in certain exemplary embodiments.

To assist with monitoring storage of the liquid L within beverage reservoir 210, controller 240 may include a timer. The timer may count down the interval during which the liquid L within beverage reservoir 210 is best for consumption. For example, when beverage reservoir 210 is filled with the liquid L, controller 240 may start the timer, and a signal may be transmitted to the user of beverage preservation assembly 200, e.g., in the form of a green LED light or similar, to notify the user that the liquid L is fit for consumption. Conversely, when the interval has elapsed, controller 240 may stop the timer, and another signal may be transmitted to the user of beverage preservation assembly 200, e.g., in the form of a red LED light or similar, to notify the user that the liquid L is no longer fit for consumption and/or should be replaced. Prior to starting the timer, controller 240 may receive an identity of the liquid L, and controller 240 may calculate or retrieve the interval. For example, an internal logic within controller 240 may be used to determine the interval and/or the length of safe storage of liquid L within beverage reservoir 210. pH sensor 270 may also be used to monitor the pH of the liquid L, and the alert may be activated if the measured pH significantly changes. Thus, pH sensor 270 may serve as an additional consumption safety check.

Figure 3:
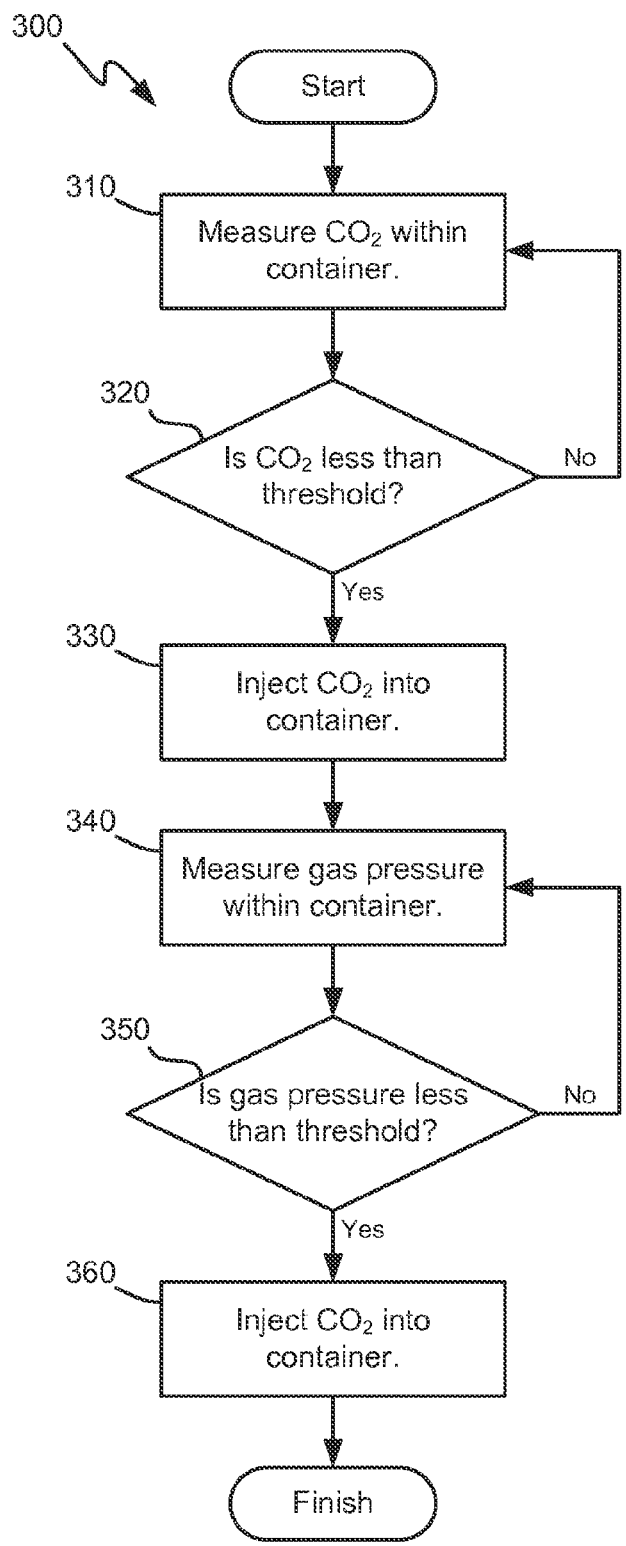
FIG. 3 illustrates a method for operating the exemplary beverage preservation assembly of FIG. 2 according to an exemplary embodiment of the present subject matter.

FIG. 3 illustrates a method 300 for operating beverage preservation assembly 200 according to an exemplary embodiment of the present subject matter. As may be seen in FIG. 3, controller 240 may measure the amount of carbon dioxide $CO_2$ with the head space above the liquid L in beverage reservoir 210 with first sensor 254 at 310. If the amount of carbon dioxide $CO_2$ is less than a threshold at 320, controller 240 may open valve 224 in order to inject carbon dioxide $CO_2$ from carbon dioxide source 220 into beverage reservoir 210 via conduit 230 at 330. In addition, controller 240 may measure the pressure of gas with the head space above the liquid L in beverage reservoir 210 with first sensor 254 at 340. If the pressure of gas within the beverage reservoir 210 is less than a threshold at 350, controller 240 may open valve 224 in order to inject carbon dioxide $CO_2$ from carbon dioxide source 220 into beverage reservoir 210 via conduit 230 at 360. In such a manner, method 300 may assist with insuring that sufficient carbon dioxide $CO_2$ is disposed within beverage dispenser 210 and that carbon dioxide $CO_2$ is injected into beverage dispenser 210 during dispensing of the liquid L from beverage dispenser 210.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A refrigerator appliance, comprising:
a casing defining a chilled chamber;
a beverage reservoir disposed within the chilled chamber of the cabinet;
a beverage preservation assembly comprising
a carbon dioxide source; and
a conduit extending between the carbon dioxide source and the beverage reservoir, an outlet of the conduit positioned at a bottom portion of the beverage reservoir,
a controller operatively coupled to the carbon dioxide source, the controller configured for activating the carbon dioxide source such that the carbon dioxide source directs carbon dioxide into the beverage reservoir via the conduit when liquid is dispensed from the beverage reservoir,
wherein the carbon dioxide source comprises a gas cartridge charged with carbon dioxide gas or a carbon dioxide generator comprising a container with yeast and sugar disposed within the container.

2. The refrigerator appliance of claim 1, further comprising a check valve mounted to the beverage reservoir at a top portion of the reservoir, the check valve configured for directing air out of the beverage reservoir.

3. The refrigerator appliance of claim 2, further comprising a membrane mounted to the beverage reservoir downstream of the check valve relative to a flow of air out of the beverage reservoir through the check valve.

4. The refrigerator appliance of claim 2, further comprising a cap removeably mounted to the beverage reservoir at the top portion of the beverage reservoir, the check valve positioned on the cap.

5. The refrigerator appliance of claim 1, wherein the beverage preservation assembly further comprises a valve coupled to the conduit, the controller operatively coupled to the valve, wherein activating the carbon dioxide source comprises opening the valve.

6. The refrigerator appliance of claim 5, wherein the beverage preservation assembly further comprises a first pressure sensor configured for measuring a gas pressure within the beverage reservoir and a second pressure sensor configured for measuring a gas pressure within the carbon dioxide source, the controller operatively coupled to the first pressure sensor and the second pressure sensor, the controller configured for closing the valve when a pressure measurement from the first pressure sensor is greater than a pressure measurement from the second pressure sensor.

7. The refrigerator appliance of claim 1, wherein the controller comprises a timer, the controller configured from measuring a storage time of liquid within the beverage reservoir and for activating an alert when the storage time of the liquid within the beverage reservoir exceeds a storage time limit.

8. The refrigerator appliance of claim 1, wherein the beverage reservoir defines an internal storage volume, the internal storage volume of the beverage reservoir being greater than one gallon.

9. The refrigerator appliance of claim 1, wherein the beverage reservoir comprises a dispenser nozzle, the dispenser nozzle configured for selectively directing liquid out of the beverage reservoir.

10. A refrigerator appliance, comprising:
a casing defining a freezer chamber and a fresh food chamber;
a beverage reservoir disposed within the fresh food chamber of the cabinet;
a beverage preservation assembly comprising
a carbon dioxide source positioned within the cabinet;
a conduit extending between the carbon dioxide source and the beverage reservoir; and
a valve coupled to the conduit,
a controller operatively coupled to the valve, the controller configured for opening the valve such that carbon dioxide from the carbon dioxide source flows into the beverage reservoir via the conduit when liquid is dispensed from the beverage reservoir,
wherein the carbon dioxide source comprises a gas cartridge charged with carbon dioxide gas or a carbon dioxide generator comprising a container with yeast and sugar disposed within the container.

11. The refrigerator appliance of claim 10, further comprising a check valve mounted to the beverage reservoir at a top portion of the reservoir, the check valve configured for directing air out of the beverage reservoir.

12. The refrigerator appliance of claim 11, further comprising a membrane mounted to the beverage reservoir downstream of the check valve relative to a flow of air out of the beverage reservoir through the check valve.

13. The refrigerator appliance of claim 11, further comprising a cap removeably mounted to the beverage reservoir at the top portion of the beverage reservoir, the check valve positioned on the cap.

14. The refrigerator appliance of claim 10, wherein an outlet of the conduit is positioned at a bottom portion of the beverage reservoir.

15. The refrigerator appliance of claim 10, wherein the beverage preservation assembly further comprises a first pressure sensor configured for measuring a gas pressure within the beverage reservoir and a second pressure sensor configured for measuring a gas pressure within the carbon dioxide source, the controller operatively coupled to the first pressure sensor and the second pressure sensor, the controller configured for closing the valve when a pressure measurement from the first pressure sensor is greater than a pressure measurement from the second pressure sensor.

16. The refrigerator appliance of claim 10, wherein the controller comprises a timer, the controller configured from measuring a storage time of liquid within the beverage reservoir and for activating an alert when the storage time of the liquid within the beverage reservoir exceeds a storage time limit.

17. The refrigerator appliance of claim 10, wherein the beverage reservoir defines an internal storage volume, the internal storage volume of the beverage reservoir being greater than one gallon.

18. The refrigerator appliance of claim 10, wherein the beverage reservoir comprises a dispenser nozzle, the dispenser nozzle configured for selectively directing liquid out of the beverage reservoir.

19. A refrigerator appliance, comprising:
a casing defining a chilled chamber;
a beverage reservoir disposed within the chilled chamber of the cabinet;
a beverage preservation assembly comprising
a carbon dioxide source; and
a conduit extending between the carbon dioxide source and the beverage reservoir, an outlet of the conduit positioned at a bottom portion of the beverage reservoir,
a controller operatively coupled to the carbon dioxide source, the controller configured for activating the carbon dioxide source such that the carbon dioxide source directs carbon dioxide into the beverage reservoir via the conduit when liquid is dispensed from the beverage reservoir,
wherein the controller comprises a timer, the controller configured from measuring a storage time of liquid within the beverage reservoir and for activating an alert when the storage time of the liquid within the beverage reservoir exceeds a storage time limit.

* * * * *